United States Patent
Van Rens

(10) Patent No.: US 10,773,277 B2
(45) Date of Patent: Sep. 15, 2020

(54) ULTRASOUND SYSTEM AND METHOD

(71) Applicant: KONINKLIJKE PHILIPS N.V., Eindhoven (NL)

(72) Inventor: Antonia Cornelia Van Rens, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 380 days.

(21) Appl. No.: 15/551,395

(22) PCT Filed: Feb. 17, 2016

(86) PCT No.: PCT/EP2016/053391
§ 371 (c)(1),
(2) Date: Aug. 16, 2017

(87) PCT Pub. No.: WO2016/139065
PCT Pub. Date: Sep. 9, 2016

(65) Prior Publication Data
US 2018/0029076 A1  Feb. 1, 2018

(30) Foreign Application Priority Data

Mar. 5, 2015 (EP) ..................................... 15157767

(51) Int. Cl.
*A61B 8/00* (2006.01)
*B06B 1/02* (2006.01)
(Continued)

(52) U.S. Cl.
CPC .......... *B06B 1/0215* (2013.01); *A61B 8/4483* (2013.01); *B06B 1/0292* (2013.01); *G01N 29/2406* (2013.01); *A61B 8/12* (2013.01)

(58) Field of Classification Search
CPC ....... A61B 8/4483; A61B 8/12; A61B 8/4494; G01N 29/2406; B06B 1/0292
See application file for complete search history.

(56) References Cited

U.S. PATENT DOCUMENTS 8,008,835 B2 * 8/2011 Degertekin ........ G01N 29/2406
310/309
2005/0200241 A1 9/2005 Degerteken
(Continued)

FOREIGN PATENT DOCUMENTS

WO  2005087391 A2  9/2005

*Primary Examiner* — Joel Lamprecht

(57) ABSTRACT

An ultrasound system (1) is disclosed that comprises a probe (10) including an array (110) of CMUT (capacitive micromachined ultrasound transducer) cells (100), each cell comprising a substrate (112) carrying a first electrode (122) of an electrode arrangement, the substrate being spatially separated from a flexible membrane (114) including a second electrode (120) of said electrode arrangement by a gap (118); a voltage supply (45) coupled to said probe and adapted to provide a first set of said CMUT cells with a sequence of drive voltages each including a bias voltage component and a stimulus component of different frequency for generating a series of temporally distinct pulses each having a different frequency, wherein each pulse is generated in a separate transmit mode and provide a second set of said CMUT cells with a sequence of temporally distinct bias voltages, wherein each temporally distinct bias voltage is provided in a receive mode following one of said transmit modes and is for setting the second set of CMUT cells to a resonance frequency corresponding to the pulse frequency of said transmit mode; and a signal processing unit (22) communicatively coupled to said array and adapted to superimpose the echo signals received by the second set of CMUT cells during the respective receive modes. An ultrasonic imaging method using such a system is also disclosed.

15 Claims, 9 Drawing Sheets

100

(51) Int. Cl.
*G01N 29/24* (2006.01)
*A61B 8/12* (2006.01)

(56) References Cited

U.S. PATENT DOCUMENTS

2005/0215909 A1 9/2005 Barnes
2010/0217124 A1 8/2010 Cooley

* cited by examiner

ULTRASOUND SYSTEM AND METHOD

This application is the U.S. National Phase application under 35 U.S.C. § 371 of International Application No. PCT/EP2016/053391, filed on Feb. 17, 2016, which claims the benefit of EP Application Serial No. 15157767.3, filed Mar. 5, 2015. These applications are hereby incorporated by reference herein.

FIELD OF THE INVENTION

The present invention relates to an ultrasound system such as an ultrasound diagnostic imaging system or an ultrasound therapeutic system comprising a probe including an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap; and a voltage supply coupled to said electrode arrangement.

The present invention further relates to an ultrasonic imaging method using such a system.

BACKGROUND OF THE INVENTION

Ultrasonic transducers used for medical imaging have numerous characteristics that lead to the production of high quality diagnostic images. Among these are broad bandwidth, affecting resolution and high sensitivity, which combined with pressure output affects depth of field of acoustic signals at ultrasonic frequencies. Conventionally the piezoelectric materials which possess these characteristics have been made of PZT and PVDF materials, with PZT being particularly popular as the material of choice. However, PZT suffers from a number of notable drawbacks. Firstly, the ceramic PZT materials require manufacturing processes including dicing, matching layer bonding, fillers, electroplating and interconnections that are distinctly different and complex and require extensive handling, all of which can result in transducer stack unit yields that are lower than desired. This manufacturing complexity increases the cost of the final transducer probe and puts design limitations on the minimum spacing between the elements as well as the size of the individual elements. Moreover, PZT materials have a poorly matched impedance to water or biological tissue, such that matching layers need to be added to the PZT materials in order to obtain the desired acoustic impedance matching with the medium of interest. As ultrasound system mainframes have become smaller and dominated by field programmable gate arrays (FPGAs) and software for much of the signal processing functionality, the cost of system mainframes has dropped with the size of the systems. Ultrasound systems are now available in inexpensive portable, desktop and handheld form, for instance for use as ultrasound diagnostic imaging systems or as ultrasound therapeutic systems in which a particular (tissue) anomaly is ablated using high-energy ultrasound pulses. As a result, the cost of the transducer probe is an ever-increasing percentage of the overall cost of the system, an increase which has been accelerated by the advent of higher element-count arrays used for 3D imaging in the case of ultrasound diagnostic imaging systems. The probes used for ultrasound 3D imaging with electronic steering rely on specialized semiconductor devices application-specific integrated circuits (ASICs) which perform microbeam forming for two-dimensional (2D) arrays of transducer elements. Accordingly it is desirable to be able to manufacture transducer arrays with improved yields and at lower cost to facilitate the need for low-cost ultrasound systems, and preferably by manufacturing processes compatible with semiconductor production.

Recent developments have led to the prospect that medical ultrasound transducers can be batch manufactured by semiconductor processes. Desirably these processes should be the same ones used to produce the ASIC circuitry needed by an ultrasound probe such as a CMOS process. These developments have produced micromachined ultrasonic transducers or MUTs, the preferred form being the capacitive MUT (CMUT). CMUT transducers are tiny diaphragm-like devices with electrodes that convert the sound vibration of a received ultrasound signal into a modulated capacitance. For transmission the capacitive charge applied to the electrodes is modulated to vibrate/move the diaphragm of the device and thereby transmit an ultrasound wave. Since these diaphragms are manufactured by semiconductor processes the devices generally can have dimensions in the 10-500 micrometer range, with the diaphragm diameter for instance being selected to match the diaphragm diameter to the desired resonance frequency (range) of the diaphragm, with spacing between the individual diaphragms less than a few micrometers. Many such individual CMUTs can be connected together and operated in unison as a single transducer element. For example, four to sixteen CMUTs can be coupled together to function in unison as a single transducer element. A typical 2D transducer array can have 2000-10000 CMUT transducer elements by way of example.

The manufacture of CMUT transducer-based ultrasound systems is therefore more cost-effective compared to PZT-based systems. Moreover, due to the materials used in such semiconductor processes, the CMUT transducers exhibit much improved acoustic impedance matching to water and biological tissue, which obviates the need for multiple matching layers and yields an improved effective bandwidth.

However, such an improved effective bandwidth is not without complications. For instance, the acoustic properties of tissue such as signal attenuation, acoustic impedance and acoustic speed are frequency dependent. Signal attenuation typically increases (linearly) with frequency. Therefore, the bandwidth of the signal reduces while penetrating the tissue. Furthermore, the frequency-dependent acoustic speeds of the various frequency components of large bandwidth transmit pulses cause aberrations that can reduce the quality of the wave front, particularly at larger depth.

In addition, using larger bandwidths also means that signal noise, originating from transducer elements and front-end electronics, is integrated over this larger bandwidth and therefore is more prominent. Next to that, large bandwidth electronic circuits typically dissipate more energy. Furthermore, signal transfer of the received echo signals across the transducer probe interconnect requires more bandwidth and is therefore more expensive.

US 2010/0217124 A1 discloses an ultrasound imaging system that includes an ultrasound probe having an array of transducer elements divided into a plurality of contiguous transmit sub-apertures. A plurality of transmitters coupled to the sub-apertures of the ultrasound transducer apply respective transmit signals to the sub-apertures at different frequencies and with delays that cause respective transmit beams emanating from the sub-apertures to overlap each other in a region of interest. A multiline beamformer coupled to the transducer elements processes signals corresponding to ultrasound echoes to output image signals. A processor receives the image signals from the multiline beamformer and outputs image data corresponding to the image signals.

However, this prior art citation does not address any of the aforementioned issues associated with low-noise high-bandwidth ultrasound imaging.

SUMMARY OF THE INVENTION

The present invention seeks to provide an ultrasound system having a CMUT transducer-based probe exhibiting improved noise and imaging characteristics over a large bandwidth.

The present invention further seeks to provide an ultrasound imaging method exhibiting improved noise and imaging characteristics over a large bandwidth.

According to an aspect, there is provided an ultrasound system comprising a probe including an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap;

a voltage supply coupled to said probe and adapted to provide a first set of said CMUT cells with a sequence of drive voltages each comprising a bias voltage component and a stimulus component having a different frequency for generating a series of temporally distinct transmit pulses each having a different frequency, wherein each transmit pulse is generated in a separate transmit mode, and to provide a second set of said CMUT cells with a sequence of temporally distinct bias voltages, wherein each temporally distinct bias voltage is provided in a receive mode following one of said transmit modes and is for setting the second set of CMUT cells to a resonance frequency corresponding to the pulse frequency of said transmit mode; and a signal processing unit communicatively coupled to said array and adapted to superimpose the echo signals received by the second set of CMUT cells during the respective receive modes.

By configuring the ultrasound system to generate a series of narrowband pulses of differing frequencies in temporally distinct transmit modes and receiving the echoes of such pulses in temporally distinct receive modes in which the CMUT cells in the receive mode are tuned to the frequency of these echoes, an effective broadband pulse echo can be generated by the superposition or summing of the echoes received by a CMUT cell in the various receive modes. This has the advantage that the transmit and receive channels of the ultrasound system may be configured to operate in a narrowband spectrum during each of the transmit and receive modes, thereby reducing noise and energy dissipation whilst maintaining broadband imaging characteristics due to the superposition of the narrowband echoes of different frequencies.

In a preferred embodiment, the bias voltage component of the drive voltage is for collapsing the respective flexible membranes of said CMUT cells in said first set onto the substrate of said cells; and/or the bias voltage is for collapsing the respective flexible membranes of said CMUT cells in said second set onto the substrate of said cells. By operating the CMUT cells in collapse mode during transmit and/or receive cycles, the ultrasound system can be operated in a particularly broad frequency bandwidth. Moreover, operating the CMUT cells in collapse mode provides improved control over the (center) resonance frequency and sensitive frequency region of the cMUT cells by means of the DC bias voltage applied to its electrode arrangement.

In an embodiment, each electrode arrangement further comprises a third electrode carried by the substrate, wherein the third electrode is located in between the first electrode and the second electrode and is electrically insulated from the first electrode by a dielectric layer, wherein the voltage supply is adapted to apply the stimulus of said drive voltage across the first and second electrodes and to apply the bias voltage component of said drive voltage to the third electrode. This embodiment is particularly suitable for relieving the peak voltage requirements of the ASIC technology used some implementations as well as to reduce electrical cross talk between elements and/or to simplify electronic implementations in some cases.

The second set of CMUT cells may comprise the first set of CMUT cells. In this embodiment, the CMUT cells involved in the transmit events may be subsequently switched to a receive mode to receive the pulse echoes of the pulses transmitted in the preceding transmit event.

In an embodiment, the ultrasound system further comprises a programmable bandpass filter in between the array and the signal processing unit, wherein the programmable bandpass filter is adapted to, during each receive mode, program the bandpass filter to a frequency range including the pulse frequency of an echo signal originating from a pulse generated in the transmit mode followed by said receive mode, said frequency range excluding at least some of the pulse frequencies of pulses transmitted during other transmit modes of said series. This has the advantage that the energy consumption and noise characteristics of the bandpass filter can be improved due to the configuration of a narrowband pass spectrum in each receive mode, because the bandpass filter does not have to be able to receive the full bandwidth covered by the various transmit pulses in a single receive mode.

In an embodiment, the ultrasound system further comprises a programmable beam forming unit in between the programmable bandpass filter and the signal processing unit, wherein the programmable beam forming unit is programmed as a function of the pulse frequency of an echo signal originating from a pulse generated in the transmit mode. Such a programmable beam forming unit for instance facilitates the (partial) compensation of frequency dependent attenuation effects by adapting frequency-dependent time-gain-control settings.

In an embodiment, the ultrasound system further comprises a programmable delay stage in between each CMUT cell and the signal processing unit, wherein the programmable delay stage of each CMUT cell in said second set is programmed as a function of the pulse frequency of an echo signal originating from a pulse generated in the transmit mode. Such a programmable delay stage for instance facilitates the (partial) compensation of aberrations caused by frequency-dependent acoustic speeds of the pulse echoes in conventional broadband imaging systems.

The voltage supply may comprise a first stage adapted to generate the bias voltage component of said drive voltage during said transmit modes, and a second stage adapted to generate the stimulus component of said drive voltage, said second stage being adapted to alter the frequency of said stimulus component in the different transmit modes order to generate the series of temporally distinct pulses each having a different frequency. The voltage supply may be further adapted to combine the bias voltage component and the stimulus component to form the sequence of drive voltages. The provision of such a multiple-stage voltage supply has the advantage that the bulk of the voltage does not have to follow the relatively rapid modulation of the stimulus such that it can be produced using a voltage generator including large smoothing capacitors, thereby reducing the amount of noise in the overall bias voltage signal component.

According to another aspect, there is provided a method of ultrasonic pulse imaging, comprising providing an array of CMUT (capacitive micromachined ultrasound transducer) cells, each cell comprising a substrate carrying a first electrode, the substrate being spatially separated from a flexible membrane including a second electrode by a gap; providing a first set of said CMUT cells with a sequence of drive voltages, each drive voltage comprising a bias voltage component and a stimulus component of a set frequency for generating a series of temporally distinct pulses each having a different frequency, wherein each pulse is generated in a separate transmit mode; providing a second set of said CMUT cells with a sequence of temporally distinct bias voltages for pre-shaping the flexible membrane of said CMUT cells in said second set, wherein each temporally distinct bias voltage is provided in a receive mode following one of said transmit modes and is for setting the second set of CMUT cells to a resonance frequency corresponding to the pulse frequency of said transmit mode; and superimposing the echo signals received by the second set of CMUT cells during the respective receive modes. This facilitates the generating of images exhibiting broadband characteristics using narrowband pulses and pulse echoes.

Each receive mode may be temporally distinct from each transmit mode. All CMUT cells of said array may be included in the second set in order to optimize receive sensitivity.

In an embodiment, the method further comprises programming a bandpass filter for filtering the received echo signals during each receive mode to a frequency range including the pulse frequency of an echo signal originating from a pulse generated in the transmit mode followed by said receive mode, said frequency range excluding at least some of the pulse frequencies of pulses transmitted during other transmit modes of said series. This ensures that only the relevant part of the full spectrum that can be covered by the CMUT cells is filtered in each receive mode cycle, thereby improving noise and energy consumption characteristics of the method.

In an embodiment, the method further comprises programming a delay stage for delaying received echo signals during each receive mode as a function of the pulse frequency of an echo signal originating from a pulse generated in the transmit mode followed by said receive mode. Such frequency-dependent delays can compensate frequency-dependent speed-induced aberrations, thereby improving the image quality of an image derived from the superimposed echoes.

The method may further comprise collapsing the flexible membrane of the CMUT cells in said first set onto the substrate of said cells in the respective transmit modes to optimize the pulse energy generated during each transmit event.

BRIEF DESCRIPTION OF THE DRAWINGS

Embodiments of the invention are described in more detail and by way of non-limiting examples with reference to the accompanying drawings, wherein FIG. 1 schematically depicts a CMUT cell of an ultrasound system according to an embodiment.

DETAILED DESCRIPTION OF THE EMBODIMENTS

Figure 1:
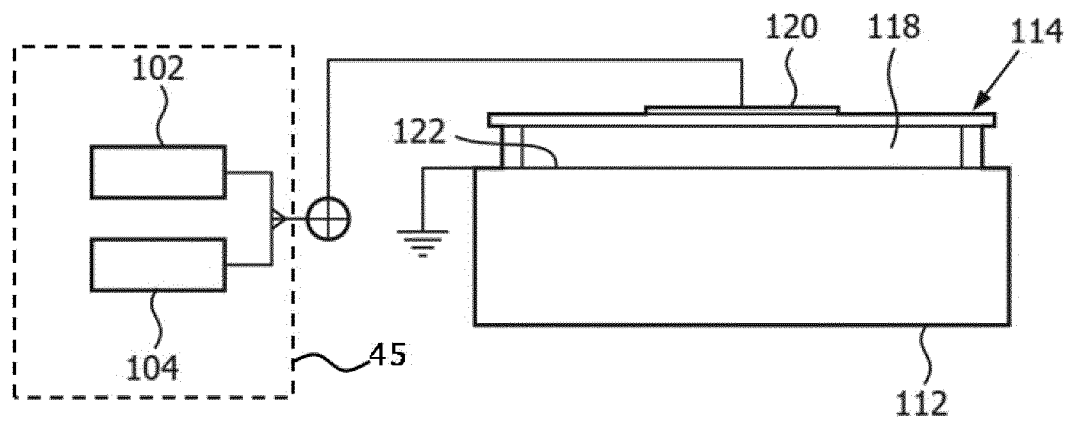

It should be understood that the Figures are merely schematic and are not drawn to scale. It should also be understood that the same reference numerals are used throughout the Figures to indicate the same or similar parts.

FIG. 1 shows an aspect of an ultrasound system according to an embodiment, in which the system includes an ultrasound probe having a transducer array comprising CMUT cells 100. As will be explained in further detail below, such an ultrasound system may be an ultrasound diagnostic imaging system in some embodiments or may be an ultrasound therapeutic system in some other embodiments. The present invention is not limited to a particular type of CMUT cells such that any suitable design of CMUT cell 100 may be contemplated. Such a CMUT cell 100 typically comprises a membrane or diaphragm 114 suspended above a silicon substrate 112 with a gap or cavity 118 there between. A top electrode 120 is located on the diaphragm 114 and moves with the diaphragm. A bottom electrode is located on the floor of the cell on the upper surface of the substrate 112 in this example. Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate layer 112 by way of non-limiting example. Other suitable arrangements, e.g. other electrode shapes and other locations of the bottom electrode 122, e.g. on the substrate layer 112 such that the bottom electrode 112 is directly exposed to the gap 118 or separated from the gap 118 by an electrically insulating layer or film to prevent a short-circuit between the top electrode 120 and the bottom electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 1 the bottom electrode 122 is grounded by way of non-limiting example. Other arrangements, e.g. a grounded top electrode 120 or both top electrode 120 and bottom electrode 122 floating are of course equally feasible. The electrodes 120, 122 are typically conductively coupled to a voltage supply 45 arranged to provide the electrode arrangement with a drive voltage having a DC bias component and an AC stimulus component of set frequency in a transmission mode, and with a DC bias voltage in a receive mode, as will be explained in more detail below. The voltage supply 45 may optionally comprise separate stages 102, 104 for providing the DC and AC components respectively, as will be explained in more detail below.

The cell 100 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell.

In an embodiment, the bottom electrode 122 is insulated on its cavity-facing surface with an additional layer (not pictured). Suitable electrically insulating layers include an oxide-nitride-oxide (ONO) dielectric layer or an oxide dielectric layer formed from tetraethyl orthosilicate formed above the substrate electrode 122 and below the membrane electrode 120 although it should be understood any electrically insulating material may be contemplated for this layer.

Exemplary techniques for producing the disclosed cavity 118 involve defining the cavity in an initial portion of the membrane layer 114 before adding a top face of the membrane layer 114. As such cavity-forming techniques are well-known per se, they will not be explained in further detail for the sake of brevity only. It should be understood that any suitable cavity-forming technique may be contemplated.

Figure 2:
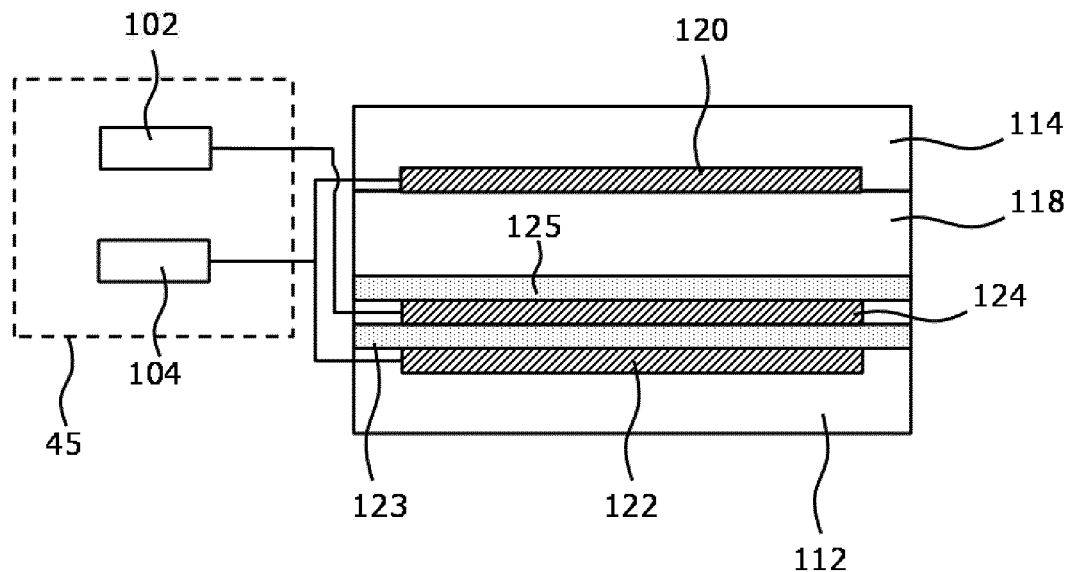
FIG. 2 schematically depicts a CMUT cell of an ultrasound system according to an alternative embodiment.

An alternative CMUT cell geometry is schematically depicted in FIG. 2, which depicts a 3-electrode CMUT cell 100. This CMUT cell 100 includes a third electrode 124 embedded into the floor of the cell 100 comprising an upper surface of the substrate 112. The bottom electrode 122 may be configured in any suitable manner, e.g. may be circularly configured and embedded into the cell floor 130.

The third electrode 124 is typically insulated on its cavity-facing surface with an upper insulating layer 125 and insulated on its bottom electrode-facing surface with a bottom insulating layer 123. Insulating layers 123 and 125 preferably are silicon dioxide ($SiO_2$) dielectric layers deposited in a TEOS-based deposition process such as a PECVD process. An alternative material for the insulating layers 123, 125 may be oxide-nitride-oxide (ONO), high-k dielectrics and oxides (aluminium oxide, various grades including silane, $SiH_4$-based PECVD $SiO_2$, and so on).

In this embodiment, the first electrode 120 and third electrode 124 of the CMUT cell 100 provide the capacitive plates that develop the actual electrical field across the of the CMUT device, whereas the capacitive coupling between the third electrode 124 and the second electrode 122 through the bottom dielectric layer 123 defines a capacitor, e.g. for a RC filter, which may be integrated in the CMUT cell 100. The first electrode 120 may be brought in vibration by means of a voltage supply 45 adapted to apply an AC stimulus with a set frequency over second electrode 122 and/or first electrode 120, which results in the generation of an acoustic beam, e.g. an acoustic pulse of a particular frequency bandwidth, whereas the third electrode 124 is provided with the DC component of the drive voltage. Third electrode 124 may be connected to a (quasi-) DC voltage by a voltage source, e.g. voltage supply 45, via a large series resistance. As a result, third electrode 124 will "see" the sum of the (quasi-)DC voltage and the RF stimulus provided to electrodes 120, 122. This implementation is particularly attractive in case the cMUT cell 100 has to be stimulated from two sides.

In the exemplary embodiments depicted in FIG. 1 and FIG. 2, the diameter of the cylindrical cavity 118 may be larger than the diameter of the circularly configured electrode plate 122. Electrode 120 may have the same outer diameter as the circularly configured electrode plate 122, although such conformance is not required. Thus, in an exemplary implementation of the present invention, the membrane electrode 120 is fixed relative to the top face of the membrane layer 114 so as to align with the electrode plate 122 below. The electrodes of the CMUT provide the capacitive plates of the device and the gap 118 is the dielectric between the plates of the capacitor. When the diaphragm vibrates, the changing dimension of the dielectric gap between the plates provides a changing capacitance which is sensed as the response of the CMUT to a received acoustic echo. The spacing between the electrodes is controlled by the application of the DC bias voltage, to the electrodes. As is known per se, by applying a static voltage above a certain threshold, the CMUT cell 100 is forced into a collapsed state in which the membrane 114 collapses onto the substrate 112. This threshold value depends on the exact design of the CMUT cell 100 and is defined as the DC bias voltage at which the membrane 114 sticks to (contacts) the cell floor by Vander Waals force during the application of the bias voltage. The amount (area) of contact between the membrane 114 and the substrate 112 is dependent on the applied bias voltage. Increasing the contact area between the membrane 114 and the substrate 112 increases the resonance frequency of the membrane 114, as will be explained in more detail with the aid of FIG. 3a and FIG. 4a.

Figure 3A:
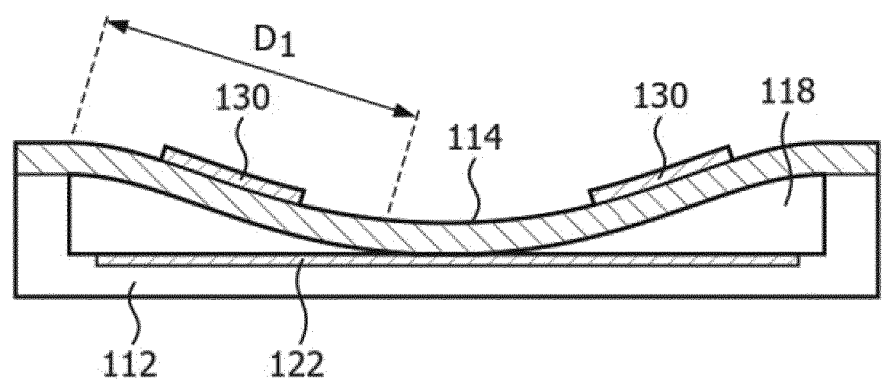
FIGS. 3A, 3B, 4A and 4B depict operating principles of such CMUT cells.

The frequency response of a collapsed mode CMUT cell 100 may be varied by adjusting the DC bias voltage applied to the CMUT electrodes after collapse. As a result, the resonance frequency of the CMUT cell increases as a higher DC bias voltage is applied to the electrodes. The principles behind this phenomenon are illustrated in FIGS. 3a, 3b, 4a and 4b. The cross-sectional views of FIGS. 3a and 4a illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 3a when a relatively low bias voltage is applied, whereas the distance D2 in FIG. 4a is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 3a will be lower than the resonant frequency of the CMUT cell in FIG. 4a which is subject to the higher pull-down bias voltage.

Figure 3B:
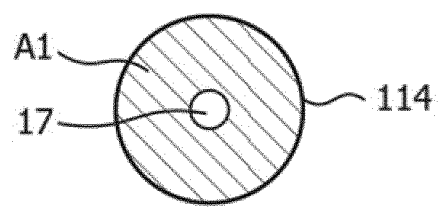
Figure 4A:
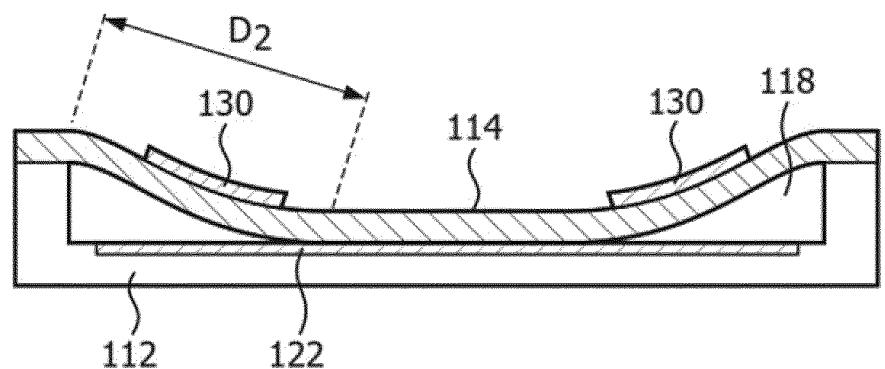
Figure 4B:
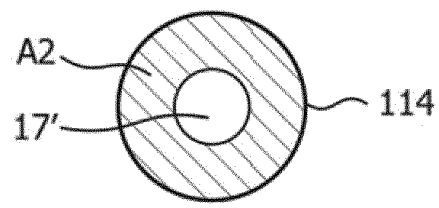

The phenomenon can also be appreciated from the two dimensional illustrations of FIGS. 3b and 4b, as it is in actuality a function of the effective operating area of the CMUT membrane. When the membrane 114 just touches the floor of the CMUT cell as shown in FIG. 3a, the effective vibrating area A1 of the non-contacting (free vibrating) portion of the cell membrane 114 is large as shown in FIG. 3b. The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage as in FIG. 4a, the greater central contact area 17' results in a lesser free vibrating area A2 as shown in FIG. 4b. This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 5:
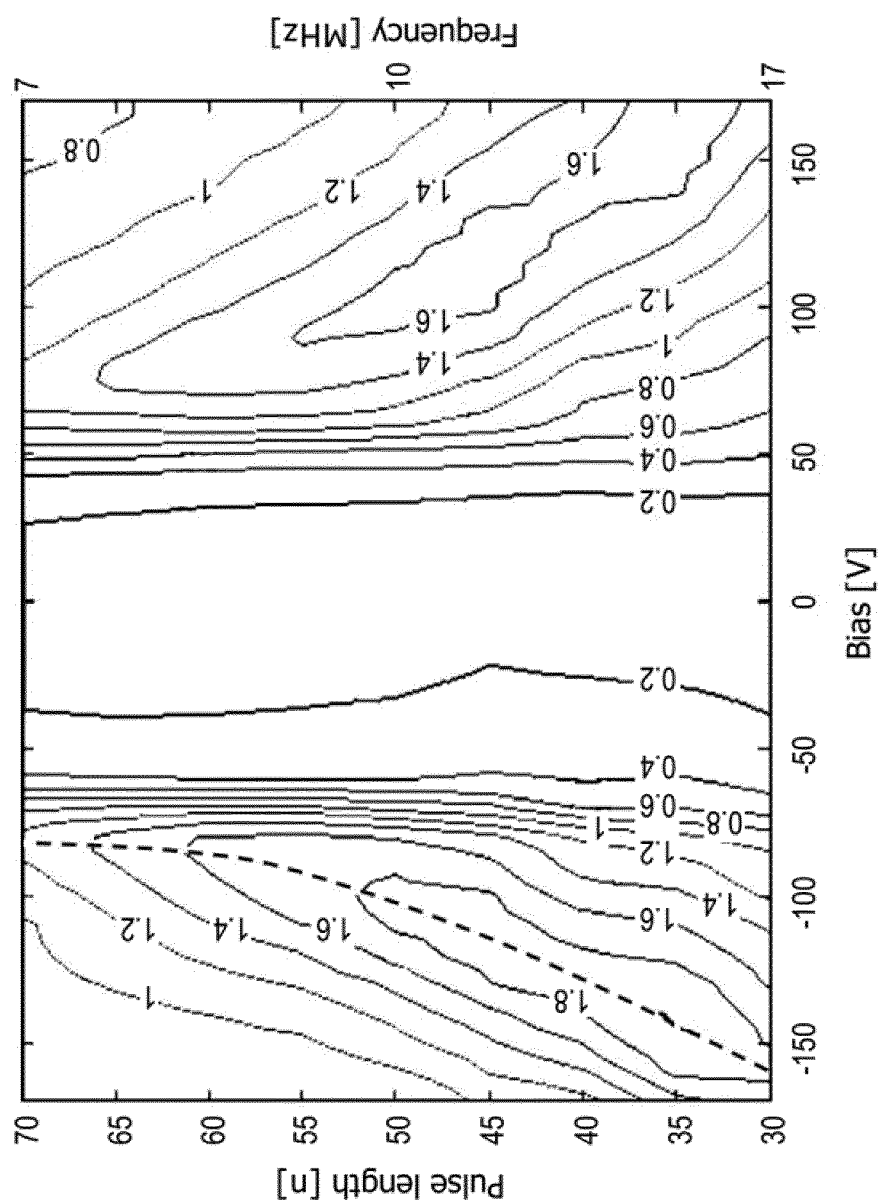
FIG. 5 is a contour plot of the acoustical performance of such CMUT cells.

FIG. 5 shows a contour plot of the acoustical pressure output of a typical CMUT cell 100 in collapse mode as a function of applied DC bias voltage with an AC stimulus having a constant frequency during transmission. The contour plot was generated using a series of substantially square uni-polar pulses with a certain duration (Tpulse length). The pressure generated by the CMUT cell 100 will be high when the resonance frequency of the CMUT cell 100 is close to the 1/(2*T_pulse length). The size of the contours indicates bandwidth. As can be seen from this contour plot, when the CMUT cell 100 is operated at a fixed or static voltage, e.g. a DC bias voltage of static value, optimal acoustic performance is obtained in an already improved frequency band compared to e.g. PZT transducer cells, but the bandwidth can be extended even further by varying the bias voltage and the stimulus frequency in a correlated manner, as indicated by the dashed line in the contour plot, such that the optimal acoustic performance of the CMUT cell 100 may be achieved over a much larger frequency range. This can be understood in back reference to FIGS. 3a and 4a, which explained that the resonance frequency of the CMUT cell 100 in a collapsed state is a function of the applied (DC) bias voltage. In the context of the present application, where reference is made to a broadband pulse or spectrum, this refers to the total spectral range of resonance frequencies and/or pulse frequencies that may be generated with the CMUT cells 100, i.e. the usable frequency range of the CMUT cells 100. It is further noted that the bandwidth range achievable by a CMUT cell 100 is not fixed and can be optimized for depending on the application in which the CMUT cells 100 are used.

Where reference is made to a narrowband pulse or spectrum, this refers to a part of the broadband spectrum such as a part that is less than half the full width of the broadband pulse or spectrum in some embodiments, e.g. a third or less, a quarter or less of the full width of the broadband pulse or spectrum and so on. Where reference is made to a broadband pulse or spectrum, this should be understood as the effective pulse or spectrum resulting from the superposition of a plurality of narrowband (TX) pulses.

In accordance with the present invention, the ultrasound imaging system is configured to utilize the broadband spectrum of the CMUT cells 100 by dividing the effective broadband spectrum, i.e. the usable frequency rangeof the CMUT cells 100 into a plurality of narrowband pulses each covering a different portion of the broadband frequency spectrum. These different portions of the spectrum may be overlapping portions having non-overlapping peak or central frequencies. For each narrowband pulse generated by one or more CMUT cells 100 in transmit mode, the pulse echo is collected by one or more CMUT cells 100 in receive mode. The pulse echo is typically processed and temporarily stored as will be explained in more detail below until all pulse echoes of the different pulses generated by the one or more CMUT cells 100 in transmit mode have been collected, after which the collected pulse echoes of the pulses originating from the same set of CMUT cells 100 are superimposed, e.g. using a signal processor, in order to generate a broadband echo, that is, the echo of a broadband pulse.

As will be explained in more detail below, this approach ensures that during each receive event, the receiver channel of the ultrasound imaging system only needs to be able to process narrowband pulse echoes, thereby improving its SNR ratio and energy consumption. To this end, the receiver channel is typically programmable to program the bandwidth characteristics of the pulse echo into the receiver channel, wherein the receiver channel is reprogrammed in between receive modes of the respective narrowband pulse echoes to retune the receiver channel to the spectral composition of the next narrowband pulse to be transmitted by the one or more CMUT cells 100 in the sequence of narrowband pulses that cover the broadband range of the CMUT cells 100.

Figure 6:
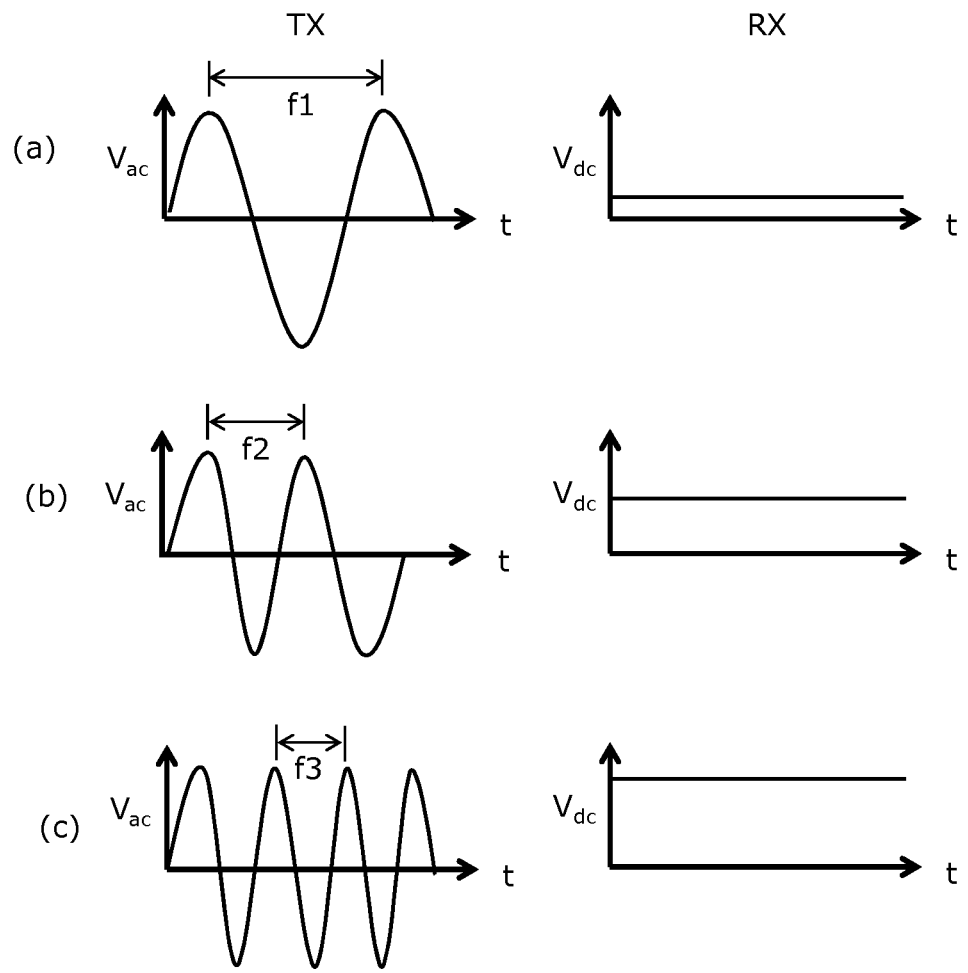
FIG. 6 schematically depicts a sequence of transmit (TX) and receive (RX) events in accordance with an embodiment.

FIG. 6 schematically depicts an example sequence of transmit and accompanying receive modes labeled (a), (b) and (c) respectively, with FIG. 6 schematically depicting the spectrum of the narrowband pulses f1, f2, f3 generated during transmit modes (a), (b) and (c) respectively. As indicated in FIG. 6, the combined spectrum F of narrowband pulses f1, f2, f3 corresponds to the desired broadband spectrum used for imaging purposes, which may be the full spectral range the CMUT cells 100 are capable of generating, or may be a part thereof. It should be understood that three narrowband pulses are shown by way of non-limiting example only; the broadband spectrum of the CMUT cells 100 may be divided into any suitable number of narrowband pulses.

Figure 7:
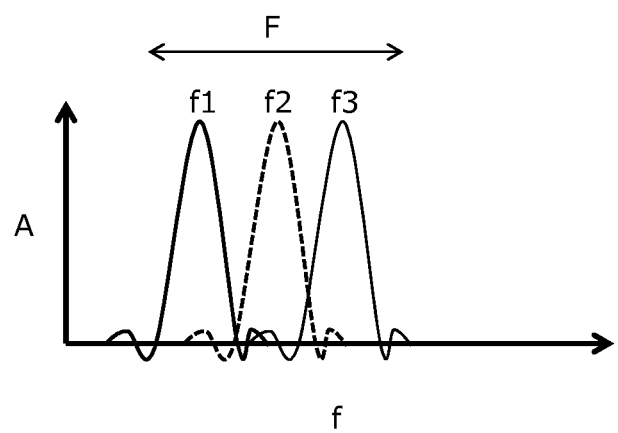
FIG. 7 schematically depicts the spectral contents of the pulses of different frequency bursts generated during the respective TX events of FIG. 6.

In a preferred embodiment, during a transmit mode, the one or more CMUT cells 100 involved in the transmission of the narrowband pulse are driven into a collapsed state in which the membrane 114 touches the floor of the CMUT cell as explained above. This may be achieved by providing the electrodes 120, 122 of the CMUT cell 100 with a DC component of the drive voltage that is sufficiently high to achieve this collapse, e.g. by means of voltage supply 45. The drive voltage provided by voltage supply 45 further comprises a frequency-dependent stimulus (Vac), which may be considered as a frequency modulation superimposed on the (quasi-)DC component of the drive voltage, as depicted in the TX modes in FIG. 6, which stimulus has a different peak or central frequency in each transmit mode. The frequency-dependent stimulus component of the drive voltage brings the membrane 114 of the CMUT cell 100 into an oscillation having an oscillation frequency corresponding to the peak or central frequency of the frequency modulation, thereby creating a transmit pulse having this peak or central frequency, as shown in FIG. 7.

As previously explained with the aid of FIG. 5, in order to optimize acoustic pressure generated by the CMUT cells 100, the area of collapse of the membrane 114 onto the floor of a CMUT cell 100 may be adjusted in a correlated manner with the frequency of the drive voltage modulation, i.e. the frequency of the stimulus, to be applied to the electrodes 120, 122 such that for each pulse frequency to be generated, the membrane 114 has a matching resonance frequency. This may be achieved by adjusting the level of the DC bias component of the drive voltage as previously explained.

Each transmit mode is typically followed by a receive mode in which a second set of CMUT cells 100 is switched to receive the pulse echoes of the pulses generated in the preceding transmit event. In a preferred embodiment, the second set of CMUT cells 100 are driven into the collapsed mode by applying a drive voltage with an appropriate DC component (Vdc) to the CMUT cells 100 (RX mode in FIG. 5). It is noted for the avoidance of doubt that FIG. 6 is merely schematic and should not be interpreted as accurately reflecting the shape of the stimulus waveform. As is well-known per se, in case of a narrow band system for instance, such stimulus signals slowly grow decrease in amplitude, such that multiple periods of the stimulus waveform are required to initiate and terminate the waveform, with the envelop shape determining the bandwidth of the stimulus. In an embodiment, in the different receive modes, different DC bias voltages may be applied to the second set of CMUT cells 100 in order to tune the area of collapse of the CMUT cells 100 such that the resonance frequency of the membrane 114 of these cells corresponds to the mean or center frequency of the transmit pulse transmitted in the preceding transmit mode, such that the receiving CMUT cells 100 exhibit optimal sensitivity to the echoes of such pulses. This is schematically depicted in FIG. 6 by the increasing DC bias voltage levels applied in the respective receive modes (a)-(c). For the sake of completeness, it is noted that the DC voltage levels of the receive modes may also be applied during the transmit modes in order to tune the resonance frequency of the membrane 114 to the pulse frequency of the transmit pulse to be generated as explained above.

It is noted at this point that although it is preferable to drive the CMUT cells 100 into collapse during transmit and receive modes, it is also feasible to operate the CMUT cells 100 in a non-collapsed mode in the transmit mode and/or the receive mode. The stimulus voltage with set frequency may be applied to the appropriate CMUT cells 100 by a signal amplifier or other suitable voltage supply 45 that generates the drive voltage as a single signal. However, in an alternative embodiment the voltage supply 45 may comprise two stages to generate different components of the drive voltage, i.e. a first stage 102 for generating the static (DC) voltage component and a second stage 104 for generating an alternating voltage component or stimulus having a set alternating frequency, which signal typically is the difference between the overall voltage and the aforementioned static component thereof. Other suitable embodiments of the voltage supply 45 should be apparent, such as for instance an embodiment in which the voltage supply 45 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage supply 45 may be implemented in any suitable manner.

Each CMUT cell 100 may be provided with a dedicated DC component and an individual frequency-dependent stimulus, e.g. provided via dedicated drive lines, or at least some of the CMUT cells 100 may be connected to a shared node for providing these CMUT cells 100 with a shared DC component and/or a shared stimulus, and so on. Many suitable configurations will be apparent to the skilled person and it is simply stipulated that any suitable configuration of the voltage supply 45 and its connections to the CMUT cells 100 may be used.

In a preferred embodiment, the static component $V_{DC}$ of the applied drive voltage meets or exceeds the threshold voltage for forcing the CMUT cells 100 into their collapsed states as previously explained. This has the advantage that the first stage 102 may include relatively large capacitors, e.g. smoothing capacitors, in order to generate a particularly low-noise static component of the overall voltage and prevent crosstalk between the different, e.g. neighboring, CMUT cells 100) which static component typically dominates the overall voltage such that the noise characteristics of the overall voltage signal will be dominated by the noise characteristics of this static component.

As will be understood from the foregoing, the respective transmit modes defining the narrowband pulses that combine to cover the broadband spectrum of the CMUT cells 100 are temporally distinct, i.e. do not overlap in time and are typically separated from each other in time by a receive mode for receiving the pulse echo of the narrowband pulse generated in the preceding transmit mode. In one extreme, a single transmit/receive cycle may comprise of a single transmit event involving a first set of CMUT cells 100, wherein the first set comprises all CMUT cells 100 of the array 110 and a single receive event involving a second set of CMUT cells 100, wherein the second set also comprises all CMUT cells 100 of the array 110. This allows for rapid imaging with limited resolution due to the fact that the interference between simultaneously transmit pulses and resulting pulse echoes may not be completely removed or compensated for during subsequent beam forming as is well-known per se.

In an opposite extreme, a single transmit/receive cycle may comprise a plurality of transmit/receive events wherein during each transmit event the first set of CMUT cells 100 consists of a single CMUT cell 100 transmitting a pulse into a medium to be imaged, wherein in the subsequent receive event all CMUT cells 100 are configured to receive echoes from this single pulse. In such an approach, a single transmit/receive cycle typically comprises a sequence of transmit/receive events in which a different CMUT cell 100 of the array 110 is selected as the transmitter until all CMUT cells 100 of the array 110 have been involved in a transmit event, analogous to synthetic aperture (SA) beam-forming. This allows for high-definition, e.g. 3-D, imaging at the expense of a slower imaging process. This approach may be preferable in scenarios where image artifacts caused by pulse (echo) interference are undesirable, as SA is typically considered to give superior resolution as retrospective beam forming is possible in both TX and RX mode and can be optimized for every location. This is typically at the expense of low TX energy levels, which results in a loss of penetration depth. This can be compensated by performing many TX events in such an SA technique and averaging the outcome, which therefore makes this approach more time-consuming.

It should be understood that number and configuration of CMUT cells 100 in a single transmit event is not particularly limited; any suitable number of CMUT cells 100, e.g. a cluster of CMUT cells 100 to increase the aperture of the transmitter as is well-known per se, may be used, although it should be understood that in at least some of these scenarios image artifacts may be difficult to avoid, as is well-known per se.

Figure 8:
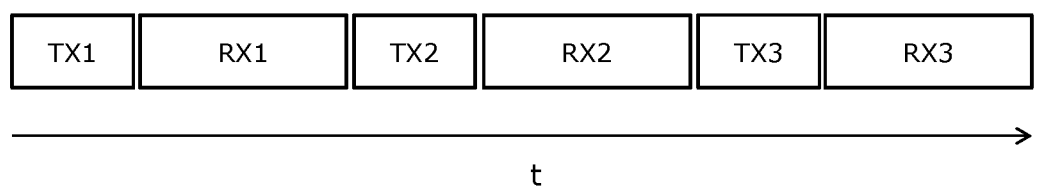
FIG. 8 schematically depicts a TX/RX sequence according to an embodiment.

In order to maximize sensitivity of the array 110 of CMUT cells 100 in receive mode, preferably all CMUT cells 100 of the array 110 are configured to receive pulse echoes. FIG. 8 schematically depicts the timeline t of such a configuration in which separate transmit cycles are interleaved with separate receive cycles that are temporally distinct from the transmit cycles and from each other; for the example pulses with frequencies f1, f2, and f3, this results in three transmit cycles TX1, TX2 and TX3 respectively, each followed by a corresponding receive cycle RX1, RX2 and RX3 for receiving the echoes of the pulses generated in transmit cycles TX1, TX2 and TX3 respectively.

Figure 9:
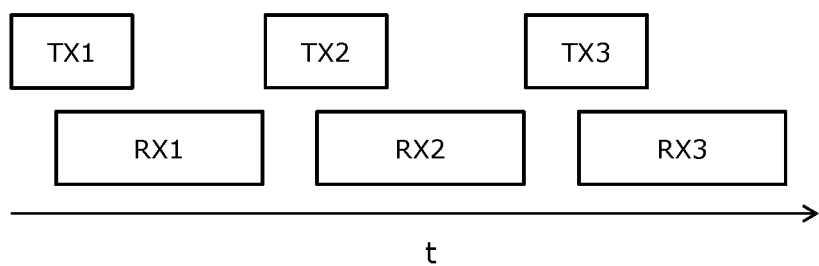
FIG. 9 schematically depicts a TX/RX sequence according to another embodiment.

It is however also feasible to configure the array 110 such that some of the CMUT cells 100 are in transmit mode whereas other CMUT cells 100 are in receive mode, thus resulting in a timeline t as schematically depicted in FIG. 9. Here, the receive cycles RX1, RX2 and RX3 are no longer temporally distinct from their corresponding TX cycles but instead at least partially overlap with these cycles. This configuration however is less preferable than the previous configuration due to the fact that the reduced number of CMUT cells 100 configured to receive pulse echoes corresponds to a reduction in the image resolution produced by the ultrasound imaging system. Furthermore, the requirements on dynamic range of the low noise amplifier are much more severe, due to the fact that receiver cells have to "listen" to echoes from the tissue while their neighbors are "shouting", i.e. transmitting signals. This embodiment is however advantageous when the system is operated in CW Doppler mode.

Figure 10:
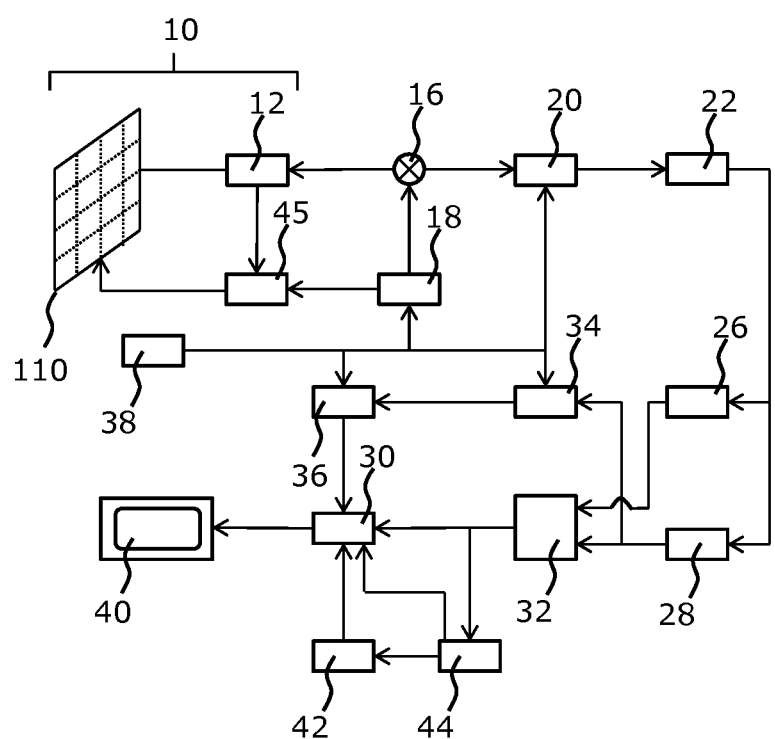
FIG. 10 schematically depicts an example embodiment of an ultrasound diagnostic system in block diagram.

In FIG. 10, an ultrasonic diagnostic imaging system with an array transducer probe according to an example embodiment of the present invention is shown in block diagram form. In FIG. 10 a CMUT transducer array 110 is provided in an ultrasound probe 10 for transmitting ultrasonic waves and receiving echo information. The transducer array 110 may be a one- or a two-dimensional array of transducer elements capable of scanning in a 2D plane or in three dimensions for 3D imaging.

The transducer array 110 is coupled to a microbeam former 12 in the probe 10 which controls transmission and reception of signals by the CMUT array cells, in particular controls the delays and apodization of these signals. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. coaxial wire, to a transmit/receive (T/R) switch 16 which switches between transmission and reception modes and protects the main beam former 20 from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control the aforementioned voltage supply 45 for the CMUT array. For instance, the voltage supply 45 sets the various DC and AC bias voltage(s) that are applied to the CMUT cells 100 of a CMUT array 110, e.g. to generate the narrowband pulses of different frequency in the respective transmission modes and to set the resonance frequencies of the CMUT cells 100 in the respective receive modes as explained above.

The partially beam-formed signals produced by the microbeamformer 12 are forwarded to the main beam former 20 where partially beam-formed signals from individual patches of transducer elements are combined into a fully beam-formed signal and digitized. For example, the main beam former 20 may have 128 channels, each of which receives a partially beam-formed signal from a patch of dozens or hundreds of CMUT transducer cells 100. In this way the signals received by thousands of transducer elements of a transducer array 110 can contribute efficiently to a single beam-formed signal.

At this point it is noted that it is of course well-known per se that the microbeam former 12 may be omitted, for instance when there is no need to reduce the number of signals to be provided from the probe 10 to the beam former 20. Microbeam formers are typically present where such a need does exists, e.g. in some 1-D and 2-D imaging architectures.

The beam-formed signals are coupled to a signal processor 22. The signal processor 22 can process the received echo signals in various ways, such as bandpass filtering, decimation, I and Q component separation, e.g. after IF mixing/demodulation, for envelop detection, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

Figure 11:
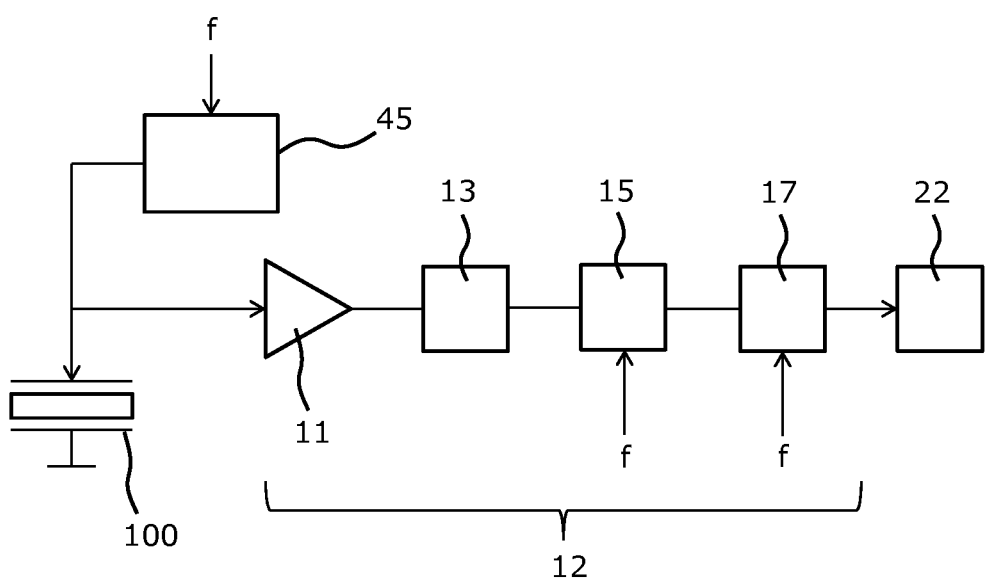
FIG. 11 schematically depicts an example aspect of the ultrasound diagnostic system of FIG. 10 in more detail.

FIG. 11 schematically depicts an aspect of a front-end of such an ultrasonic diagnostic imaging system 1 according to an example embodiment. The aspect of FIG. 11 depicts a single CMUT cell 100 of the array 110 coupled to a programmable voltage supply 45 as previously explained. The programmable voltage supply 45 is typically programmed with a control signal f that sets the appropriate frequency of the stimulus component of the drive voltage applied to the CMUT cell 100 in a transmit mode and/or sets the level of the DC bias voltage applied to the CMUT cell 100 in a transmit mode and/or a receive mode as previously explained. The front-end further comprises a receive channel including a signal amplifier 11 such as a low-noise amplifier, a time-gain controller 13, a bandpass filter 15 and a beam former 17 inking the signals of multiple CMUT cells 100 together.

In an embodiment, the time-gain controller 13 may be configurable such that the time-gain control settings of the time-gain controller 13 may be adjusted in accordance with the different narrowband pulses echoes to be received by the CMUT cell 100. In this manner, frequency-dependent attenuation of the different narrowband echoes can be at least partially compensated for. It will be readily understood that such a time-gain controller 13 may also be used in the transmission path of the CMUT cell 100 and adjusted in accordance with the different frequencies of the narrowband transmit pulses.

In an embodiment, the bandpass filter 15 is a programmable bandpass filter of which the pass frequency band is configurable. For example, the centre frequency of this passband and optionally the width of the passband may be programmable as is known per se. Consequently, the bandpass filter 15 may be configured using the frequency information signal f to set the bandpass frequency range in accordance with the frequency of the pulse echo to be received by the CMUT cell 100. This allows for the bandpass filter 15 to operate a passband that is wide enough for the pulse echo to pass through the filter, but is substantially narrower than the full broadband spectrum that the CMUT cell 100 is capable of producing. As will be readily understood by the skilled person, the bandpass filter 15 is typically reconfigured prior to each receive mode RX1, RX2, RX3 to tune the passband of the bandpass filter 15 to the appropriate frequency of the narrowband pulse echo be received. This therefore facilitates the use of a narrowband bandpass filter 15 that has superior noise characteristics and energy consumption compared to a broadband bandpass filter having a passband corresponding to the full frequency range of the CMUT cell 100. In an embodiment, the bandpass filter 15 is located downstream from an analog to digital converter (not shown), such that the bandpass filter 15 operates in the digital domain. It will be readily understood that such a bandpass filter 15 may also be used in the transmission path of the CMUT cell 100 to filter the narrowband transmit pulses in the same manner.

In an embodiment, the beam former 17 may be configured using frequency-dependent parameters as indicated by the symbolic input fin order to compensate for frequency-dependent aberrations, i.e. frequency-dependent acoustic speeds of the pulse echoes are received by the CMUT cell 100. The beam former 17 for instance may comprise a configurable delay stage in which the amount of delay added to the incoming pulse echoes may be configured such that the frequency-dependent variation of the acoustic speeds of the different pulse echoes can be reduced or eliminated by the appropriate configuration of these delay stages. It will be readily understood that such a beam former 17 may also or alternatively be used in the transmission path of the CMUT cell 100 to delay the narrowband transmit pulses in the same manner.

The thus formed respective pulse echo beams of different frequency may be superimposed by the signal processor 22 in order to form a broadband pulse echo from the respective superimposed narrowband components. To this end, the signal processor 22 may include or have access to a data storage element (not shown) such as a suitable memory device or the like, in which individual narrowband pulse echoes are temporarily stored until all narrowband components of the broadband pulse echo have been collected, after which the signal processor 22 may retrieve the stored pulse echoes from the data storage element for the aforementioned superposition of the individual narrowband echoes to form the broadband echo. It is noted that such superposition of individual pulse echoes is well-known per se; this technique for instance is routinely used in synthetic aperture beam-forming approaches and will therefore not be explained in further detail for the sake of brevity only. It is simply noted that any suitable superposition algorithm may be employed by the signal processor 22.

At this point, it is noted that although the various components of the receive channel in FIG. 11 are shown as discrete components in a particular order, it should be understood that this is by way of non-limiting example only and that these components may be re-ordered as suitable and at least some of these components may be combined. For example, the signal processor 22 may also implement additional functions such as a digital bandpass filter 15 and/or a beam former 17 as previously explained. Similarly, the superposition of pulse echoes may be performed by any suitable processor in the diagnostic imaging system 1, such as the signal processor 22 or the image processor 38. Other variations will be immediately apparent to the skilled person.

Figure 12:
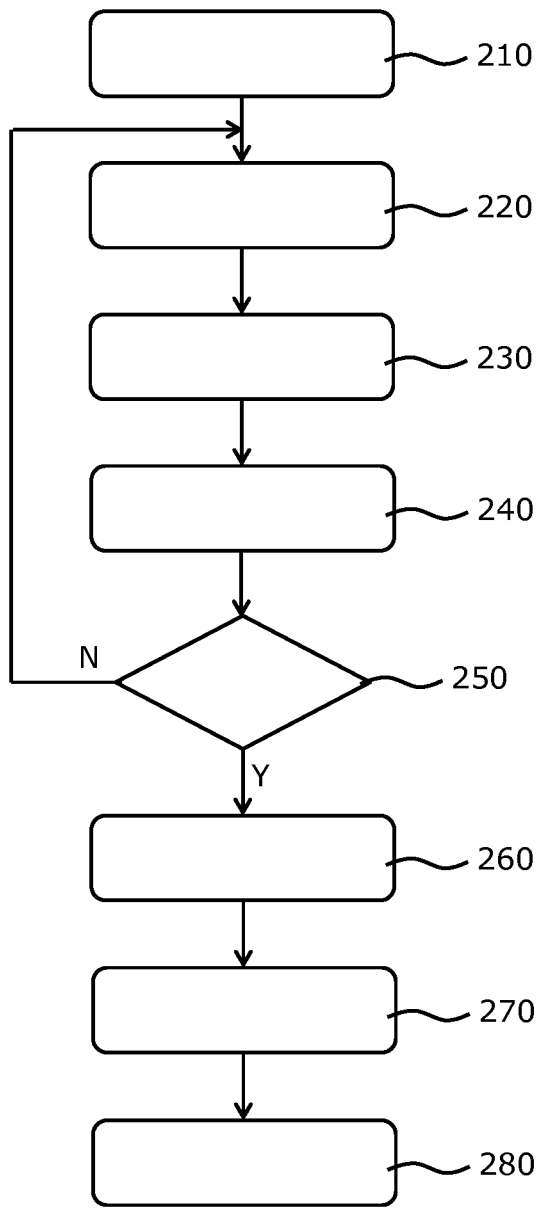
FIG. 12 is a flow chart of an ultrasound imaging method according to an embodiment.

FIG. 12 is a flow chart of an ultrasonic imaging method 200 employed by the ultrasound system according to embodiments of the present invention, such as the example embodiment of the ultrasound diagnostic imaging system 1 as shown in FIG. 10. The method 200 starts in step 210 after which the method proceeds to step 220 in which the electrode arrangements of a first set of CMUT cells 100, e.g. a single cell or a cluster of cells, is provided with a frequency dependent drive voltage having a DC component and a frequency-dependent, i.e. AC, stimulus as previously explained, which causes the first set of CMUT cells 100 to transmit a pulse of this particular frequency into a medium of interest, e.g. tissue of a patient, in step 230.

Next, the method may proceed by switching to a reception mode in step 250 in which the pulse echoes are received as previously explained, e.g. using a subset of CMUT cells 100 of the transducer array 110 not used for transmission or alternatively by operating the CMUT cells 100 previously used for transmitting the narrowband pulses in reception mode. In an embodiment, this may involve providing the second set of CMUT cells 100 involved in the reception of the pulse echoes with a DC bias voltage to drive the CMUT cells 100 in a collapsed mode such that the resonance frequency of the respective membranes 114 of the CMUT cells 100 corresponds to the main or centre frequency of the narrowband pulse generated in the preceding transmit mode.

In step 250, it is checked if all narrowband components of the broadband spectrum of the CMUT cells 100 have been generated by the respective narrowband pulses. If this is not the case, the method refers back to step 220 in which the next transmit mode is initiated by providing the first set of CMUT cells 100 with a drive voltage having a frequency-adjusted stimulus as previously explained. It is reiterated that the DC component of this bias voltage may also be adjusted such that the resonance frequency of the membrane 114 matches the frequency of the frequency modulation, i.e. of the pulse to be generated, in order to maximize acoustic performance of the CMUT cell 100 as previously explained with the aid of FIG. 4.

Once all narrowband components of the broadband spectrum of the CMUT cells 100 have been generated in this fashion, as checked in step 250, the method proceeds to step 260 in which the respective narrowband pulse echoes as received during the discrete receive modes of respective steps 240 are superimposed to create a broadband pulse echo as previously explained. The thus generated superimposed broadband pulse echoes may be subsequently processed in step 270 in order to generate an ultrasound image. As the processing of such ultrasound echoes is well-known per se, this will not be explained in further detail for the sake of brevity only. It suffices to say that any suitable ultrasound echo processing technique may be applied. Following the generation of such an ultrasound image, the method may terminate in step 280.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound system comprising:
a probe including an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap;
a voltage supply coupled to said probe and adapted to:
provide the respective electrode arrangements of a first set of said CMUT cells with a sequence of drive voltages each including a bias voltage component and a stimulus having a different frequency for generating a series of temporally distinct pulses each having a different frequency, wherein each pulse is generated in a separate transmit mode;
provide the respective electrode arrangements of a second set of said CMUT cells with a sequence of temporally distinct bias voltages, wherein each temporally distinct bias voltage is provided in a receive mode following one of said transmit modes and is for setting the second set of CMUT cells to a resonance frequency corresponding to the pulse frequency of said transmit mode; and
a signal processing unit communicatively coupled to said array and adapted to superimpose echo signals received by the second set of CMUT cells during the respective receive modes.

2. The ultrasound system of claim 1, wherein:
the bias voltage component of the drive voltage is for collapsing the respective flexible membranes of said CMUT cells in said first set onto the substrate of said cells; and/or
the bias voltage is for collapsing the respective flexible membranes of said CMUT cells in said second set onto the substrate of said cells.

3. The ultrasound system of claim 1, wherein each electrode arrangement further comprises a third electrode carried by the substrate, wherein the third electrode is located in between the first electrode and the second electrode and is electrically insulated from the first electrode by a dielectric layer, wherein the voltage supply is adapted to apply the stimulus of said drive voltage across the first and second electrodes and to apply the bias voltage component of said drive voltage to the third electrode.

4. The ultrasound system of claim 1, wherein the second set of CMUT cells comprises the first set of CMUT cells.

5. The ultrasound system of claim 1, further comprising a programmable bandpass filter in between the array and the signal processing unit, wherein the programmable bandpass filter is adapted to, during each receive mode, program the bandpass filter to a frequency range including the pulse frequency of an echo signal originating from a pulse generated in the transmit mode followed by said receive mode, said frequency range excluding at least some of the pulse frequencies of pulses transmitted during other transmit modes of said series.

6. The ultrasound system of claim 5, further comprising a programmable beam forming unit in between the programmable bandpass filter and the signal processing unit, wherein the programmable beam forming unit is programmed as a function of the pulse frequency of an echo signal originating from a pulse generated in the transmit mode.

7. The ultrasound system of claim 1, further comprising a programmable delay stage in between each CMUT cell and the signal processing unit, wherein the programmable delay stage of each CMUT cell in said second set is programmed, in each receive mode, as a function of the pulse frequency of an echo signal originating from a pulse generated in the transmit mode.

8. The ultrasound system of claim 1, wherein the voltage supply is adapted to collapse the flexible membrane of the CMUT cells in said first set onto the substrate of said cells in the respective transmit modes.

9. The ultrasound system of claim 8, wherein the voltage supply comprises:
  a first stage adapted to generate the bias voltage component of said drive voltage during said transmit modes, wherein the bias voltage component is sufficient to collapse the flexible membrane of said CMUT cells in first set onto the substrate of said cells; and
  a second stage adapted to generate the stimulus component of said drive voltage, said second stage being adapted to alter the frequency of said stimulus component in the different transmit modes order to generate the series of temporally distinct pulses each having a different frequency.

10. A method of ultrasonic pulse imaging, comprising:
providing an array of CMUT (capacitive micromachined ultrasound transducer) cells, each cell comprising a substrate carrying a first electrode, the substrate being spatially separated from a flexible membrane including a second electrode by a gap;
providing a first set of said CMUT cells with a sequence of drive voltages for generating a series of temporally distinct pulses each having a different frequency, wherein each drive voltage comprises a bias voltage component and a stimulus component of different frequency, and wherein each pulse is generated in a separate transmit mode;
providing a second set of said CMUT cells with a sequence of temporally distinct bias voltages, wherein each temporally distinct bias voltage is provided in a receive mode following one of said transmit modes and is for setting the second set of CMUT cells to a resonance frequency corresponding to the pulse frequency of said transmit mode; and
superimposing echo signals received by the second set of CMUT cells during the respective receive modes.

11. The method of claim 10, wherein each receive mode is temporally distinct from each transmit mode.

12. The method of claim 10, wherein the second set comprises all CMUT cells of said array.

13. The method of claim 10, further comprising programming a bandpass filter for filtering the received echo signals during each receive mode to a frequency range including the pulse frequency of an echo signal originating from a pulse generated in the transmit mode followed by said receive mode, said frequency range excluding at least some of the pulse frequencies of pulses transmitted during other transmit modes of said series.

14. The method of claim 10, further comprising programming a delay stage for delaying received echo signals during each receive mode as a function of the pulse frequency of an echo signal originating from a pulse generated in the transmit mode followed by said receive mode.

15. The method of claim 10, further comprising collapsing the flexible membrane of the CMUT cells in said first set onto the substrate of said cells in the respective transmit modes.

* * * * *